United States Patent
Kim et al.

(10) Patent No.: US 10,362,941 B2
(45) Date of Patent: Jul. 30, 2019

(54) METHOD AND APPARATUS FOR PERFORMING REGISTRATION OF MEDICAL IMAGES

(71) Applicant: Samsung Electronics Co., Ltd., Suwon-si (KR)

(72) Inventors: Jung-bae Kim, Hwaseong-si (KR); Young-kyoo Hwang, Seoul (KR); Do-kyoon Kim, Seongnam-si (KR); Won-chul Bang, Seongnam-si (KR); Young-taek Oh, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 552 days.

(21) Appl. No.: 14/177,897

(22) Filed: Feb. 11, 2014

(65) Prior Publication Data
US 2014/0235998 A1    Aug. 21, 2014

(30) Foreign Application Priority Data
Feb. 21, 2013    (KR) .................. 10-2013-0018833

(51) Int. Cl.
*A61B 5/00*    (2006.01)
*A61B 6/00*    (2006.01)
(Continued)

(52) U.S. Cl.
CPC ............ *A61B 5/0035* (2013.01); *A61B 5/113* (2013.01); *A61B 6/5247* (2013.01); (Continued)

(58) Field of Classification Search
CPC .................................................. A61B 5/0035
See application file for complete search history.

(56) References Cited

U.S. PATENT DOCUMENTS 6,473,635 B1 * 10/2002 Rasche .................... A61B 5/06
                                                                600/424
7,835,785 B2    11/2010 Scully et al.
(Continued)

FOREIGN PATENT DOCUMENTS

CN    1737819 A    2/2006
CN    101248441 A    8/2008
(Continued)

OTHER PUBLICATIONS

Blackall, Jane M., et al. "Alignment of Sparse Freehand 3-D Ultrasound With Preoperative Images of the Liver Using Models of Respiratory Motion and Deformation." IEEE Transactions on Medical Imaging 24.11 (Nov. 2005): pp. 1405-1416.
(Continued)

*Primary Examiner* — Rochelle D Turchen
(74) *Attorney, Agent, or Firm* — Cha & Reiter, LLC

(57) ABSTRACT

A method and apparatus for performing registration of medical images includes mapping a virtual coordinate system used by a first medical apparatus and a virtual coordinate system used by a second medical apparatus to one another. The coordinate systems are associated with a real-time medical image captured by the first medical apparatus and a three-dimensional (3D) medical image previously captured by the second medical apparatus, respectively. The method further includes detecting a position of a probe of the first medical apparatus from a coordinate system used by the second medical apparatus, based on a result of the mapping, determining a volume image corresponding to the detected position of the probe from the previously captured 3D medical image, and extracting from the determined volume image a cross-sectional image corresponding to the real-time medical image, where the real-time medical image changes according to a patient's physical movement.

15 Claims, 11 Drawing Sheets

(51) Int. Cl.
  *A61B 8/08* (2006.01)
  *A61B 5/113* (2006.01)
  *G06T 7/33* (2017.01)
  *A61B 90/00* (2016.01)

(52) U.S. Cl.
  CPC .............. *A61B 8/5261* (2013.01); *G06T 7/33* (2017.01); *A61B 2090/364* (2016.02); *G06T 2200/04* (2013.01); *G06T 2207/10081* (2013.01); *G06T 2207/10088* (2013.01); *G06T 2207/10132* (2013.01); *G06T 2207/30056* (2013.01)

(56) References Cited

U.S. PATENT DOCUMENTS

| 8,306,297 | B2 | 11/2012 | Fu et al. | |
|---|---|---|---|---|
| 2007/0010743 | A1* | 1/2007 | Arai | A61B 8/13 600/443 |
| 2008/0130825 | A1 | 6/2008 | Fu et al. | |
| 2010/0174192 | A1* | 7/2010 | Azuma | A61B 6/5247 600/443 |
| 2012/0035462 | A1 | 2/2012 | Maurer, Jr. et al. | |
| 2012/0245453 | A1* | 9/2012 | Tryggestad | A61B 6/463 600/413 |

FOREIGN PATENT DOCUMENTS

| EP | 1 847 294 A1 | 10/2007 |
|---|---|---|
| JP | 2008-188193 | 8/2008 |
| JP | 2012-091042 | 5/2012 |
| KR | 10-2010-0089704 | 8/2010 |
| WO | WO 2007/002926 A2 | 1/2007 |
| WO | WO 2009/053896 A2 | 4/2009 |

OTHER PUBLICATIONS

Extended European Search Report issued by the European Patent Office dated Apr. 22, 2014 in European Patent Application No. EP 14 15 6028. (6 Pages in English).

Chinese Office Action dated Oct. 9, 2017 in corresponding Chinese Patent Application No. 201410054332.8 (31 pages in English and 19 pages in Chinese).

* cited by examiner

METHOD AND APPARATUS FOR PERFORMING REGISTRATION OF MEDICAL IMAGES

CROSS-REFERENCE TO RELATED APPLICATIONS

This application claims the benefit under 35 U.S.C. 119(a) of Korean Patent Application No. 10-2013-0018833 filed on Feb. 21, 2013, in the Korean Intellectual Property Office, the entire disclosure of which is incorporated herein by reference for all purposes.

BACKGROUND

1. Field

The present disclosure relates to methods and apparatuses for performing registration of medical images.

2. Description of Related Art

With recent developments in medical technology, high definition medical images may be acquired and fine manipulation of medical equipment, such as by medical devices, has become possible. Accordingly, a method of treating a patient by directly forming a small hole in his or her skin, inserting a catheter or a medical needle into the patient's body through the small hole, and observing the interior of the patient's body by using medical imaging equipment introduced into the interior of the body through the catheter or medical needle is being actively developed. Such a method may be referred to as a medical treatment method using an image or an interventional image medical treatment method. In such an approach, a medical practitioner recognizes the position of an organ or a lesion through an image provided using this technology. In addition, the medical practitioner may observe a change in the position of an organ or a lesion according to the patient's breathing or movement during a medical treatment. Thus, the medical practitioner needs to be able to accurately and quickly recognize the breathing or moving based on real-time medical imagery. However, it is difficult to clearly identify the shapes of an organ and a lesion from a real-time medical image with the naked eye. In contrast to an ultrasonic wave image, a magnetic resonance (MR) image or a computed tomography (CT) image may clearly distinguish the position and shape of an organ and a lesion. However, since an MR or CT image may not be acquired in real-time during a medical treatment, the breathing and moving of a patient during the medical treatment may not be reflected in such an image.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Provided are methods, apparatuses, and systems for performing registration of a real-time medical image captured by a first medical apparatus and a three-dimensional (3D) medical image previously captured by a second medical apparatus to reflect changes according to the patient's physical movement.

In one general aspect, a method of performing registration of medical images includes mapping a virtual coordinate system used by a first medical apparatus and a virtual coordinate system used by a second medical apparatus to each other, wherein the virtual coordinate systems are associated with a real-time medical image captured by the first medical apparatus and a three-dimensional (3D) medical image previously captured by the second medical apparatus, respectively, detecting a position of a probe of the first medical apparatus in a virtual coordinate system used by the second medical apparatus, based on a result of the mapping, determining a volume image, corresponding to the detected position of the probe, from the previously captured 3D medical image, and extracting from the determined volume image a cross-sectional image corresponding to the real-time medical image, wherein the cross-sectional image changes according to a patient's physical movement.

The method may further provide that in the extracting of the cross-sectional image, the cross-sectional image is updated when a scanning plane of the probe is relatively moved inside the patient's body according to the patient's physical movement.

The determining of the volume image may include estimating a relative movement range of a scanning plane of the probe according to the patient's physical movement when the probe remains still, and determining a size of the volume image from the 3D medical image based on the estimated movement range.

The determining of the volume image may include selecting a cross-section corresponding to a scanning plane of the probe from the 3D medical image by using a coordinate value of the detected position, and selecting a reference cross-section and cross-sections neighboring the reference cross-section from the 3D medical image.

The determining of the volume image may further include reconstructing the volume image by accumulating the reference cross-section and the cross-sections neighboring the reference cross-section.

The mapping of the virtual coordinate systems may include generating a first cross-sectional image of the real-time medical image, selecting a two-dimensional (2D) medical image corresponding to the first cross-sectional image among a plurality of 2D medical images forming the 3D medical image based on an anatomical feature appearing in the first cross-sectional image, and generating a coordinate conversion function to convert the coordinate system used by the first medical apparatus to the coordinate system used by the second medical apparatus based on the selected 2D medical image and the first cross-sectional image.

The detecting of the position of the probe may include receiving a coordinate value of the probe that is moved in a coordinate system used by the first medical apparatus, when the probe is moved, and converting the coordinate value of the probe that is moved to a coordinate value of the coordinate system used by the second medical apparatus, by using the mapping result.

The extracting of the cross-sectional image may include extracting the cross-sectional image based on a similarity between anatomical features appearing on the real-time medical image and the determined volume image.

The extracting of the cross-sectional image may include performing segmentation on each of anatomical objects appearing on the real-time medical image and the volume image, and extracting from the volume image a cross-section having a largest similarity between the anatomical objects segmented in the real-time medical image and the volume image.

The extracting of the cross-sectional image may include acquiring a real-time medical image that changes in a state when the probe remains still is acquired, and extracting the cross-sectional image considering an anatomical feature appearing on the acquired real-time medical image.

In another general aspect, a non-transitory computer-readable storage medium stores a program for performing registration of medical images, the program comprising instructions for causing a computer to carry out the method described above.

In another general aspect, an apparatus for performing registration of medical images includes a coordinate conversion device configured to map a virtual coordinate system used by a first medical apparatus and a virtual coordinate system used by a second medical apparatus to each other and to detect a position of a probe of the first medical apparatus in the virtual coordinate system used by the second medical apparatus based on a result of the mapping, a volume image determination device configured to determine a volume image corresponding to the detected position from a 3D medical image that is previously captured, and an image output device configured to extract from the determined volume image a cross-sectional image corresponding to a real-time medical image captured by the first medical apparatus that changes according to a patient's physical movement.

The cross-sectional image may be updated when a scanning plane of the probe is relatively moved inside the patient's body according to the patient's physical movement.

The volume image determination device may estimate a relative movement range of a scanning plane of the probe according to the patient's physical movement when the probe remains still, and may determine a size of the volume image from the 3D medical image based on the estimated movement range.

The volume image determination device may select a cross-section corresponding to a scanning plane of the probe from the 3D medical image by using a coordinate value of the detected position, and may select a reference cross-section and cross-sections neighboring the reference cross-section from the 3D medical image.

The apparatus may further include a model reconstruction device configured to reconstruct the volume image by accumulating the reference cross-section and the cross-sections neighboring the reference cross-section.

The apparatus may further include a 2D image selection device that is configured to generate a first cross-sectional image of the real-time medical image and to select a 2D medical image corresponding to the first cross-sectional image among a plurality of 2D medical images forming the 3D medical image based on an anatomical feature appearing in the first cross-sectional image, wherein the coordinate conversion device generates a coordinate conversion function to convert a coordinate system used by the first medical apparatus to the coordinate system used by the second medical apparatus based on the selected 2D medical image and the first cross-sectional image.

The apparatus may provide that, when the probe is moved, the coordinate conversion device receives a coordinate value of the probe that is moved in a coordinate system used by the first medical apparatus, and converts the coordinate value of the probe that is moved to a coordinate value of the coordinate system used by the second medical apparatus, by using the mapping result.

The image output device may extract the cross-sectional image based on a similarity between anatomical features appearing on the real-time medical image and the determined volume image.

The apparatus may further include an image segmentation device configured to perform segmentation on each of anatomical objects appearing on the real-time medical image and the volume image, wherein the image output device extracts from the volume image a cross-section having a largest similarity between the anatomical objects segmented in the real-time medical image and the volume image.

The apparatus may further include a real-time medical image acquisition device configured to acquire the real-time medical image captured by the first medical apparatus.

In another general aspect, a medical image registration system includes a pre-treatment medical imagery apparatus configured to generate a set of pre-treatment medical images of a volume of interest of a patient, a real-time medical imagery apparatus configured to generate a treatment medical image in real-time of a volume of interest of the patient, and a medical image registration apparatus configured to perform registration between the set of pre-treatment medical images and the treatment medical image.

The pre-treatment medical images may have at least one of a higher signal-to-noise ratio or a higher edge contrast than the treatment medical image.

The medical image registration apparatus may perform the registration by mapping a virtual coordinate system of the set of pre-treatment medical images and a virtual coordinate system the treatment medical image to each other.

The treatment medical image may be generated and updated in real-time based on a probe that emits and receives an ultrasonic wave.

The medical image registration apparatus may perform the registration in consideration of a change in the real-time medical image according to the patient's physical movement in a state when the probe is in a still state.

The medical image registration apparatus may perform the registration in consideration of a change in the real-time medical image according to the physical motion of the probe.

Other features and aspects will be apparent from the following detailed description, the drawings, and the claims.

Figure 1:
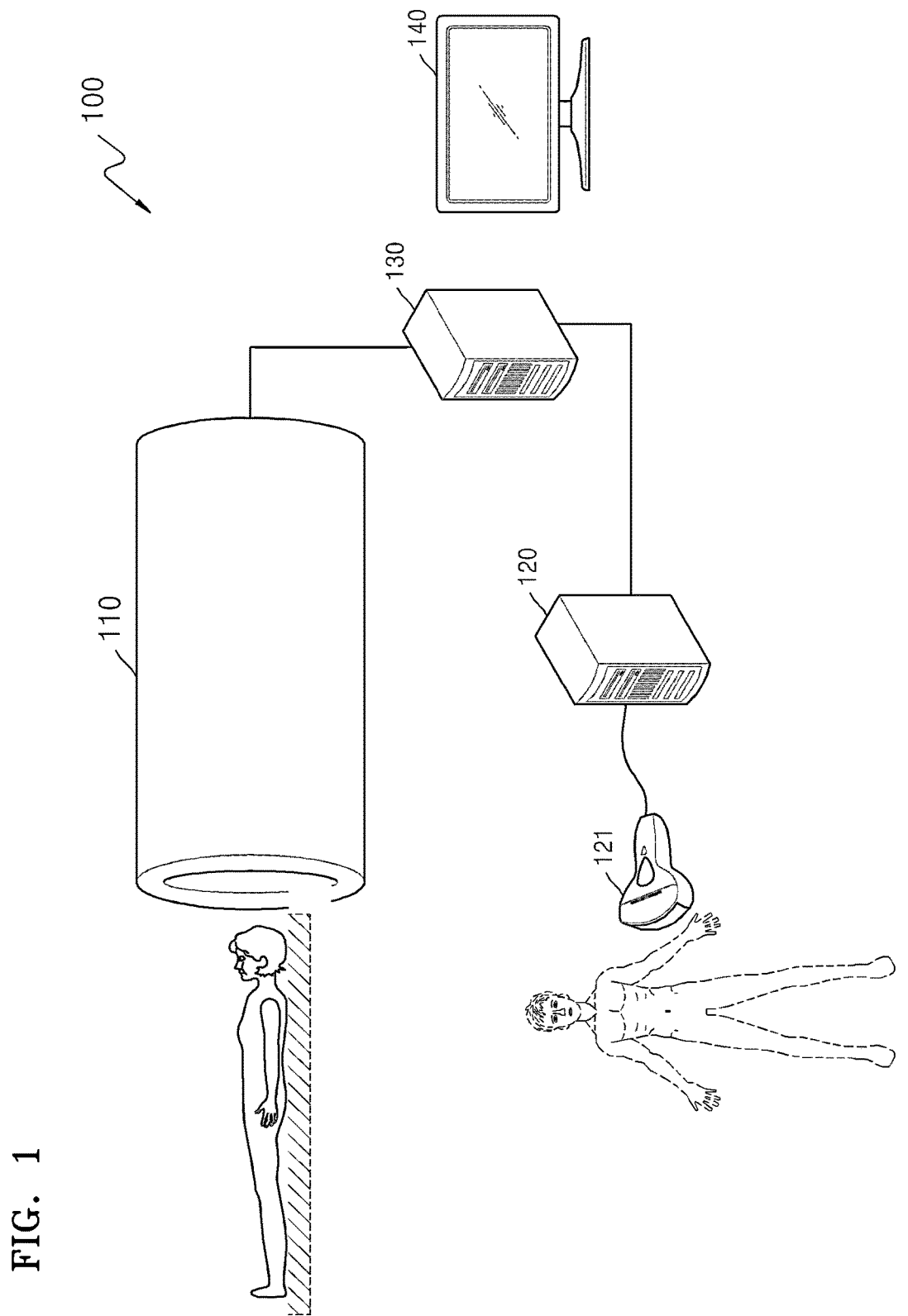
FIG. 1 illustrates a structure of a medical image registration system, according to an example embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As used herein, the term "and/or" includes any and all combinations of one or more of the associated listed items. Expressions such as "at least one of," when preceding a list of elements, modify the entire list of elements and do not modify the individual elements of the list. As used herein, the phrase "relatively moved" is used to refer to a case in which an item moves with relation to a point of reference, where the point of reference itself may not move. For example, as scanned organs move inside a patient's body during respiration and change position with respect to a probe that remains still, the scanned organs are "relatively moved" with respect to the probe.

FIG. 1 illustrates a structure of a medical image registration system 100, according to an example embodiment. Referring to FIG. 1, the medical image registration system 100 according to the present embodiment includes a first medical apparatus 120, a second medical apparatus 110, a medical image registration apparatus 130, and an image display apparatus 140.

The second medical apparatus 110 generates a set of second medical images with respect to a volume of interest (VOI) of an object before a medical treatment. The set of second medical images serves as a set of reference images that provides high-quality reference images that provide information about the contents of the VOI to help interpret lower-quality real-time images. In an example, the second medical apparatus 110 is configured as any one of a computed tomography (CT) imaging apparatus, a magnetic resonance (MR) imaging apparatus, an X-ray imaging apparatus, and a positron emission tomography (PET) imaging apparatus.

However, these are merely examples of the second medical apparatus 110, and other potential imaging apparatuses may be used, or multiple types of imaging apparatus may be used together in a combination. In the following description, for convenience of explanation, it is assumed that second medical images are MR images or CT images. A CT image or an MR image generated by the second medical apparatus 110 has the feature that it clearly distinguishes a position of an organ and a position of a lesion. However, the CT or MR image may not reflect real-time changes that occur as a patient breathes or moves during a medical treatment. Such real-time changes potentially deform or change a position of an organ, and because they occur in real-time, technologies such as CT or MR imagery are not well-adapted to reflect such changes. The reason for not being able to reflect such real-time changes differs for each technology. In the case of a CT image that is a capturing method using radioactive rays, taking images in real-time leads to the possibility that a patient and a medical practitioner are exposed to the radioactive rays for a long time, which may present a health risk to the patient and the medical practitioner. In the case of an MR image, the length of time necessary to capture an individual image is a long time, so it is not realistic to be able to capture MR images in real-time.

The first medical apparatus 120 provides a medical image in real-time with respect to a VOI of an object. In an example, the first medical apparatus 120 is formed of an ultrasonography machine for generating a real-time medical image in the interventional medical treatment process with respect to the interior of a patient. The first medical apparatus 120 irradiates an ultrasonic wave signal to an area of interest, such as to a volume in the interior of the patient, by using a probe 121 communicatively connected to the first medical apparatus, and detects a reflected ultrasonic wave signal to generate an ultrasonic wave image.

Such an ultrasonic wave image is generated based on the principle that different arrangements and types of materials in the VOI will reflect the ultrasonic wave signal differently, and by analyzing the characteristics of the reflected ultrasonic waves, it is possible to produce an image that is representative of the contents of the VOI. This principle will be discussed further, below. The probe 121 may be communicatively connected to the first medical apparatus using a wired or wireless connection. The probe 121 is generally formed of a piezoelectric transducer, which converts electrical energy into an ultrasonic wave and vice versa.

When an ultrasonic wave of a few megahertz (MHz) to several hundred MHz is transmitted to a particular area inside the patient's body from the probe 121, the ultrasonic wave is partially reflected, such as from boundaries between various different tissues. In particular, the ultrasonic wave is reflected from where there is a change in density in the inside of a patient's body, for example, blood cells in blood plasma or small structures in organs. The reflected ultrasonic wave vibrates the piezoelectric transducer of the probe 121 and the piezoelectric transducer outputs electrical pulses according to the vibrations. Thus, the piezoelectric transducer operates to convert electrical energy to output an ultrasonic wave, but then subsequently receives reflected ultrasonic energy and converts the received reflected ultrasonic energy into a signal that includes electric pulses representative of the reflected ultrasonic energy. Once generated by the piezoelectric transducer in response to the reflected ultrasonic energy, the electrical pulses are converted into image data.

As described above, in an example, although a first medical image such as an ultrasonic image is acquired in real-time by the first medical apparatus 120, since the ultrasonic images may be low-quality images due to the nature of ultrasonic imagery, the first medical image may include much noise. Such noise makes it difficult to identify an outline, an internal structure, or a lesion of an organ. For example, since a lesion and a peripheral tissue have a similar reflection characteristic in response to ultrasonic wave energy, a contrast at a boundary between a lesion and a peripheral tissue in an ultrasonic wave image, that is, an edge contrast of an object, is relatively low. For example, when there is low edge contrast, it is difficult to differentiate between which portions of the image correspond to a lesion and which portions correspond to a peripheral tissue. Thus, even though ultrasonic wave images may be obtained in real-time, it may be difficult to use the images to determine where boundaries in the images are located. Also, noise and artifacts exist due to interference and diffusion of ultrasonic waves as they travel through the patient and are reflected. Therefore, although the ultrasonic wave medical image is acquired faster than an MR or CT image, providing real-time imagery, an organ and a lesion that are distinguishable in the MR or CT image, may not be clearly distinguished from the peripheral tissue in the ultrasonic wave medical image because a signal to noise ratio (SNR) and the edge contrast of an object in the ultrasonic wave medical image are low.

In an embodiment, the medical images captured by the first and second medical apparatuses 120 and 110 are two-dimensional (2D) sectional images. However, the embodiment may generate a three-dimensional (3D) medical image by accumulating the 2D sectional images. For example, the second medical apparatus 110 captures a plurality of sectional images by changing the location and orientation of each sectional image. As discussed above, these sectional images are captured prior to treatment. When the sectional images are accumulated, image data of a 3D volume showing a particular portion of a patient's body in 3D is generated based on using appropriate techniques to combine the 2D sectional images. The above method of generating image data of a 3D volume by accumulating sectional images is referred to as a multiplanar reconstruction (MPR) method. Various specific approaches and algorithms may be used to perform such an MPF method. In particular, one approach operations such that although each of the second medical images is a 2D image, each of the pixels of an image in the second medical image has a depth value associated with it. In other words, the second medical images define a collection of voxels. Thus, a 3D model of a VOI may be generated by accumulating the second medical images, because the second medical images, when combined, define sufficient information to mode a VOI using a 3D model. Hereinafter, a set of the second medical images captured by the second medical apparatus 110 that is processed using MPR to yield information about a 3D volume is referred to as a 3D medical image.

The medical image registration apparatus 130 performs registration between a set of the second medical images acquired from the second medical apparatus 110 and a first medical image acquired from the first medical apparatus 120. By performing registration, the medical image registration apparatus 130 is able to establish a correspondence between the first medical image and the second medical images, to take advantage of the real-time nature of the first medical image and the higher quality of the second medical images. In an embodiment, registration of the first and second medical images includes a process of matching virtual coordinate systems respectively used by the first and second medical apparatuses 120 and 110 when managing the images. In such an embodiment, the registered medical image produced by the medical image registration apparatus 130 is a medical image acquired by overlaying the first and second medical image or by arranging the first and second images parallel to each other. As discussed, such overlaying and arranging may use virtual coordinate systems to help determine how to orient the images with respect to one another. The medical image registered by the medical image registration apparatus 130 is displayed by the image display apparatus 140.

The first and second medical apparatuses 120 and 110 use different virtual coordinate systems. The medical image registration apparatus 130 may perform registration of the medical images captured by the first and second medical apparatuses 120 and 110 by mapping the different virtual coordinate systems of the first and second medical apparatuses 120 and 110 to one another. 3-axis position information (x, y, z) and 3-axis rotation information (roll, pitch, yaw) are used together to determine a section from which a medical image is captured in the virtual coordinate systems used by the first and second medical apparatuses 120 and 110. Thus, aligning virtual coordinate systems requires determining a translation and a rotation that cause the virtual coordinate systems to align. For example, a position in a 3D space where a medical image is captured is specified by the virtual coordinate systems used by the first and second medical apparatuses 120 and 110. For an MR or CT image, coordinate values of a virtual coordinate system are used in a process of selecting a section to be captured by the second medical apparatus 110. That is, when an MR or CT image is obtained, the MR or CT image must be set to correspond to a certain set of axes as discussed above, and hence the coordinate values are inherent to capturing each image by the second medical apparatus 110. Thus, the coordinate values of the medical image captured by the second medical apparatus 110 are identified with no additional sensing.

However, in the first medical apparatus 120, the position of a section to be captured varies according to a movement of the probe 121. In an embodiment, the probe 121 is moved not by the control of the first medical apparatus 120, but by the control of a medical operator. Accordingly in such an embodiment, in order to identify where a medical image captured by the first medical apparatus 120 is located in a virtual coordinate system, the movement of the probe 121 is sensed. Various approaches allow the first medical apparatus 120 to sense the movement of the probe 121. For example, to sense the movement of the probe 121, one approach is a method of sensing a change in a magnetic field by using a magnetic tracker in the probe 121 or and another approach is a method of sensing an optical change with an infrared or color camera by attaching an optical marker to the probe 121. However, these are merely examples and other ways of sensing the movement of the probe 121 to establish a virtual coordinate system for the first medical image may be used.

The first and second medical apparatuses 120 and 110 generally use different 3D coordinate systems, and thus, a section 1011 in a coordinate system used by the first medical apparatus 120 is specified by using the 3-axes position information (x, y, z) of a position B1 and the 3-axes rotation information (roll, pitch, yaw) of the probe 121. Once this information is available, it becomes possible to relate the separate 3D coordinate systems to one another.

In an embodiment, the real-time medical image signifies the first medical image captured by the first medical apparatus 120, whereas the 3D medical image signifies a set of the second medical images captured by the second medical apparatus 110. As discussed above, the real-time medical image is of lower quality than the 3D medical image, but the 3D medical image does not change over time. To take into account changes in the patient's body, such as due to breathing, the medical image registration apparatus 130 periodically updates the real-time medical image captured by the first medical apparatus 120. The 3D medical image previously captured by the second medical apparatus 110 is assumed to be previously stored in the medical image registration apparatus 130.

According to the present embodiment, the virtual coordinate systems used by the first medical apparatus 120 and the second medical apparatus 110 may be mapped to one another using a method described below. When the virtual coordinate systems are mapped to one another, the position of the probe 121 of the first medical apparatus 120 is detected from the virtual coordinate system used by the second medical apparatus 110. Thus, the movement of the probe 121 is tracked in the 3D medical image captured by the second medical apparatus 110, based on the mapping and the tracking approaches discussed above and a cross-sectional image corresponding to the movement of the probe 121 is provided based on the tracked movement of the probe 121.

Correspondingly, when the probe 121 is moved, the real-time medical image changes and a cross-sectional image corresponding to the changed real-time medical image is extracted from the 3D medical image. Accordingly, the real-time medical image and the 3D medical image are synchronized with each other, once the mapping has occurred.

However, when the probe 121 is not moved, the real-time medical image may be continuously changed according to the patient's physical movement. For example, organs move or change form due to breathing of a patient and even when the probe 121 stands still with respect to the patient, the real-time medical image still changes as organs and other interior constituents of the patient move.

Figure 11:
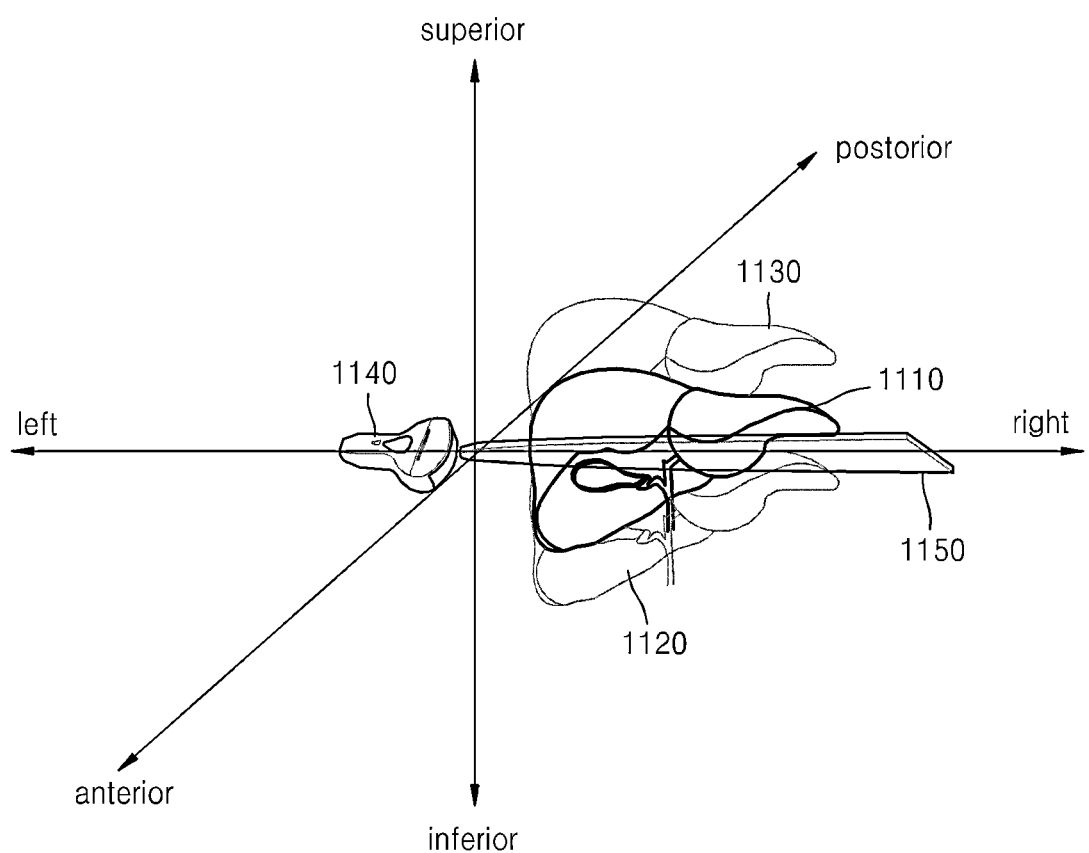
FIGS. 11 and 12 illustrate a change of a real-time medical image according to the patient's physical movement, according to an example embodiment.

Referring to FIG. 11, while being located in an intermediate state between inhalation and exhalation, a liver 1110 moves in a direction toward a legend "inferior" in an inhalation state to be located at a position 1120 and in a direction toward a legend "superior" in an exhalation state to be located at a position 1130. As a result, although an ultrasound scanning plane 1150 of a probe 1140 does not physically move, a real-time medical image captured by the probe 1140 is changed by breathing, because the liver 1110 being scanned still changes with respect to the location of the probe 1140. In other words, as a relative positional relationship between the ultrasound scanning plane 1150 and the liver 1110 changes, a real-time medical image changes, even though the probe 1140 is static.

The medical image registration apparatus 130, in an embodiment, performs registration of a real-time medical image and a 3D medical image in consideration of a change in the real-time medical image according to the patient's physical movement in a state when the probe 121 of the first medical apparatus 120 is in a still state. For example, when the real-time medical image signifies an inhalation state, a cross-sectional image corresponding to the inhalation state is extracted from the 3D medical image and then registered with the real-time medical image. When the real-time medical image signifies an exhalation state, a cross-sectional image corresponding to the exhalation state is extracted from the 3D medical image and then registered with the real-time medical image. Hence, by performing this registering, even though an organ moves due to respiration, the registering allows inference of which high-quality image of the organ as it moves.

Thus, the method of performing registration of medical images according to an embodiment may be largely classified into two methods. The first method is a method of performing registration taking into account a physical movement of the probe 121, and second, a method of performing registration taking into account a relative movement of an ultrasound scanning plane according to the patient's physical movement in a state when the probe 121 remains still.

Figure 2:
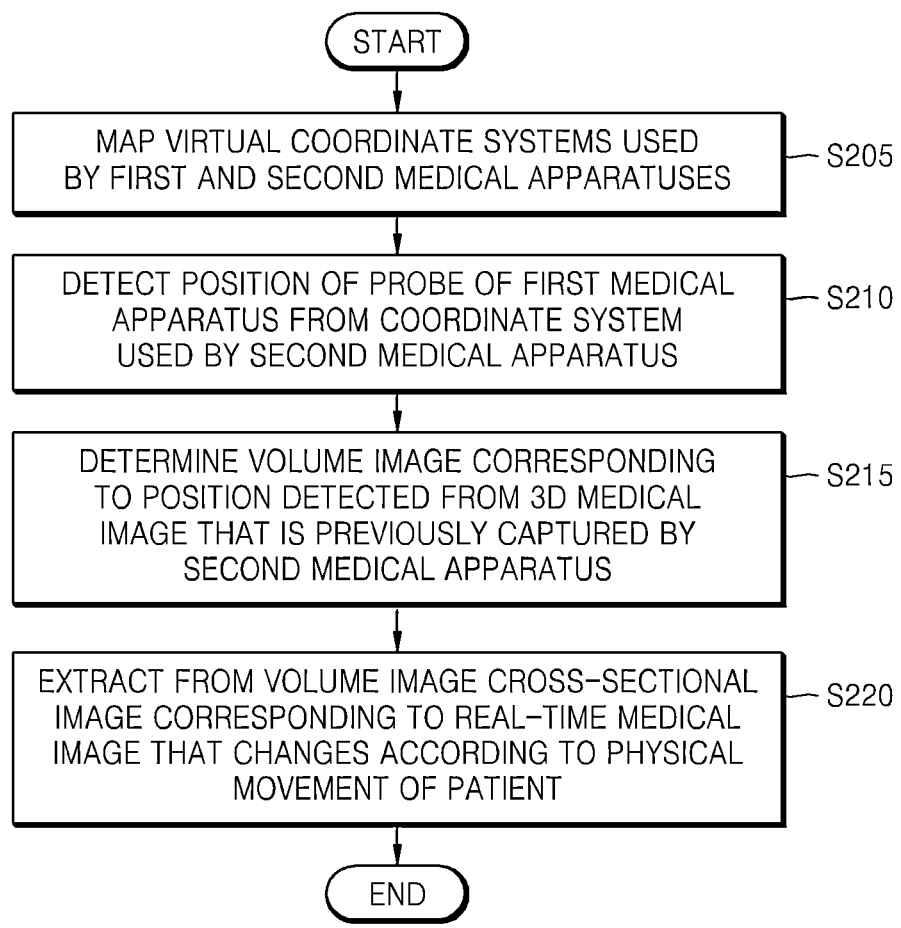
FIG. 2 is a flowchart for explaining a medical image registration method, according to an example embodiment.

FIG. 2 is a flowchart for explaining a medical image registration method according to an example embodiment. Referring to FIG. 2, in operation S205, the method maps the virtual coordinate systems used by the first medical apparatus 120 and the second medical apparatus 110 to one another by using the real-time medical image captured by 120 and the 3D medical image previously captured by the second medical apparatus 110. For example, the medical image registration apparatus 130 matches a first coordinate system that is the virtual coordinate system used by the first medical apparatus 120 and a second coordinate system that is the virtual coordinate system used by the second medical apparatus 110.

Figure 3:
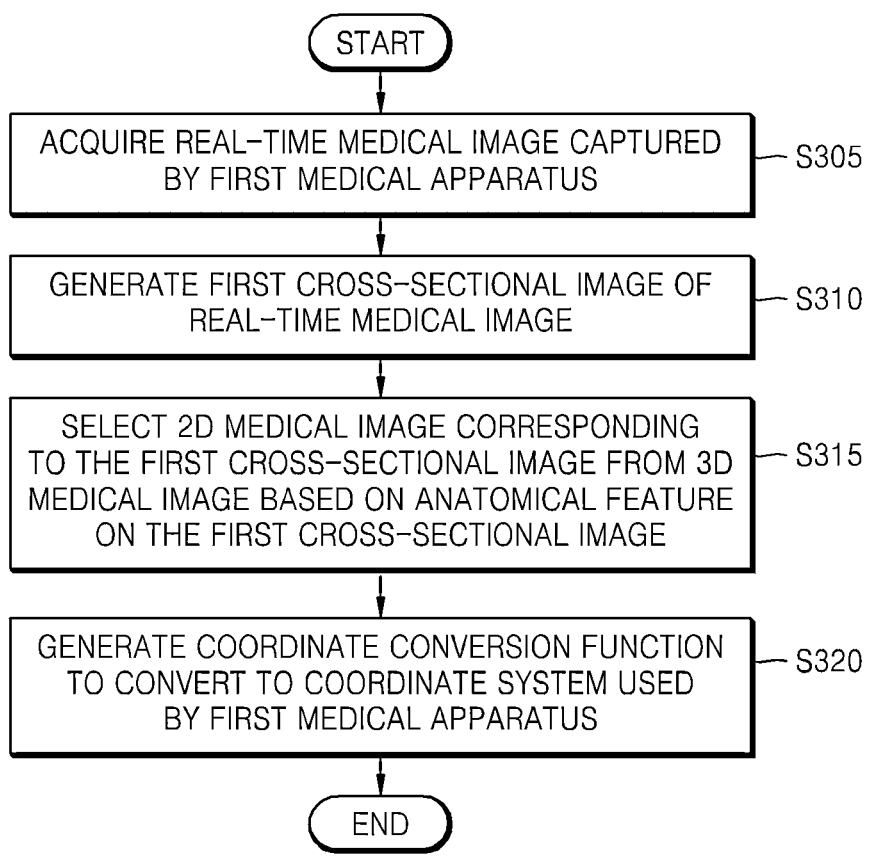
FIG. 3 is a flowchart for explaining a process of mapping virtual coordinate systems used by a first medical apparatus and a second medical apparatus, according to an example embodiment.

Operation S205 is described in detail with reference to FIG. 3. Referring to FIG. 3, at operation S305 the method acquires the real-time medical image captured by the first medical apparatus 120. The acquired real-time medical image is subsequently continuously updated. The medical image registration apparatus 130 acquires a coordinate value with respect to a position where the probe 121 is located in the first coordinate system when acquiring the real-time medical image.

Figure 10:
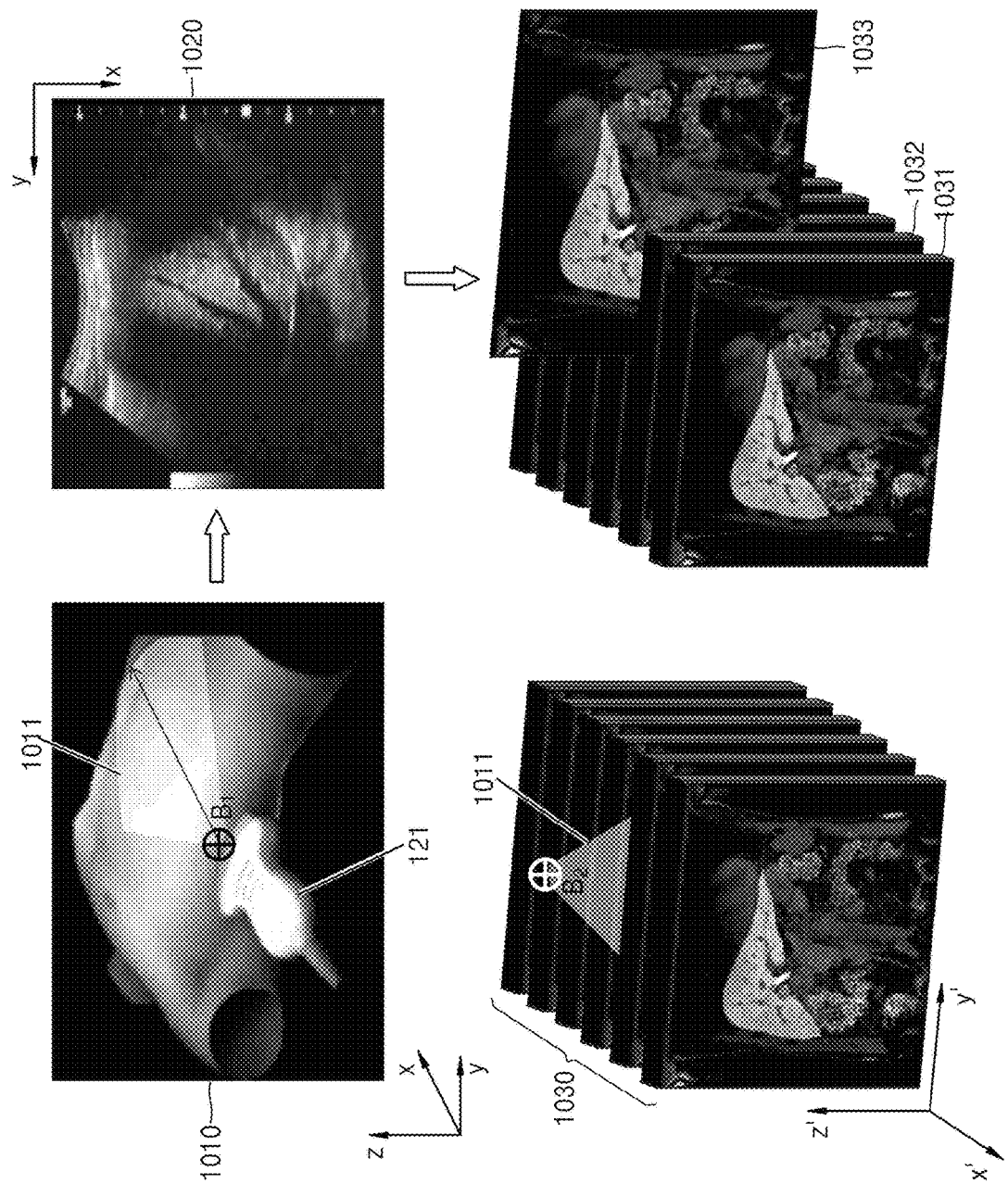
FIG. 10 is a set of medical images in a plane matching process in a medical image registration method, according to an example embodiment.

In operation S310, the method generates a first cross-sectional image of the real-time medical image. In this operation, for example, the real-time medical image changes according to a movement of the probe 121 or the patient's physical movement, such as movement due to breathing. Accordingly, the first cross-sectional image of the real-time medical image is generated to acquire a still image. The first cross-sectional image is generated such that an orientation in which the first cross-sectional image is captured is parallel to an orientation in which the second medical images forming the 3D medical images are captured. Aligning the orientations in this way improves accuracy in the detection of a 2D medical image corresponding to the first cross-sectional image from the 3D medical image, as described below. For example, a user inputs a generation command of the first cross-sectional image through the first medical apparatus 120 or the medical image registration apparatus 130. In FIG. 10, an image 1020 is the first cross-sectional image that is generated by the process described above and a plane 1011 is an ultrasound scanning plane of the probe 121 corresponding to this first cross-sectional image that is generated.

In operation S315, the method selects a 2D medical image corresponding to the first cross-sectional image from among a plurality of 2D medical images that form the 3D medical image, based on an anatomical feature of the first cross-sectional medical image. To do so, the medical image registration apparatus 130 compares the anatomical feature of the first cross-sectional image and an anatomical feature of the 2D medical images forming the 3D medical image. As a result of the comparison, the medical image registration apparatus 130 detects a 2D medical image having the largest similarity with the first cross-sectional image from the 3D medical image. Referring to FIG. 10, a 3D medical image 1030 includes a plurality of 2D medical images. The medical image registration apparatus 130 detects a 2D medical image 1033 having the largest similarity with respect to the anatomical feature with the first cross-sectional image 1020 from the 3D medical image 1030.

In operation S315, further, the method 130 segments an anatomical object in the first cross-sectional image and an anatomical object in the 3D medical image. The anatomical object may be a part of a human body, such as organs, blood vessels, lesions, and bones, or boundaries between organs. In an example, the first cross-sectional image provides a distinguishable view of the anatomical object. Here, segmentation refers to separation of an anatomical object from a background image and its parts from one another. Segmentation information about the anatomical object to be segmented may be input to the medical image registration apparatus 130 in advance, based on known characteristics of how certain tissues tend to appear in medical imagery. As one example, for an ultrasonic wave medical image, information indicating that a blood vessel has a darker brightness value in the ultrasonic wave medical image than a background is input in advance. In another example, information about anatomical features, for example, a diaphragm, which is a plane having a curvature of a predetermined value or lower, and an inferior vena cava, which is a blood vessel having a diameter of about 10 mm or higher, is input in advance. Such information characterizes aspects of anatomical features such as their shapes, sizes, and positioning.

In some embodiments, the medical image registration apparatus 130 performs segmentation by using a graph cut method or a Gaussian mixture model (GMM) method.

According to the graph cut method, the medical image registration apparatus 130 gradually extends areas of a seed point of a background and a seed point of an anatomical object by using a seed value of a background and a seed value of an anatomical object. In this manner, the medical image registration apparatus 130 segments the anatomical object by ascertaining a boundary where a background area and the area of an anatomical object meet, since the background and the anatomical object are extended in the gradual extension process until they establish the boundary between the background and the anatomical object.

According to the GMM method, the medical image registration apparatus 130 uses a color histogram of a medical image, in which the color histogram is expressed by a plurality of Gaussian distribution models. Then, the medical image registration apparatus 130 segments anatomical objects by selecting a Gaussian distribution model in a particular band of the histogram, such that the model defines boundaries between anatomical objects.

A variety of segmentation methods other than the above-described methods may be adopted in the medical image registration apparatus 130. However, the graph cut method and the Gaussian mixture model (GMM) method are only examples of candidate methods for performing segmentation. Other embodiments may use different methods for performing segmentation that provide results that are similar to the graph cut method and the Gaussian mixture model discussed above.

The medical image registration apparatus 130 calculates a similarity between the anatomical object segmented in the first cross-sectional image and the anatomical object segmented in the 3D medical image, using the segmentation approaches discussed above. For example, the medical image registration apparatus 130 expresses using a numerical measure of similarity how similar the anatomical objects observed and segmented in the first cross-sectional image are, compared to those observed and segmented in the 2D medical images forming the 3D medical image.

As an example, the medical image registration apparatus 130 calculates the similarity by using a Gabor wavelet method or a local binary pattern matching method.

According to the Gabor wavelet method, the medical image registration apparatus 130 filters anatomical objects using Gabor filters having a variety of different filtering characteristics. The medical image registration apparatus 130 compares the results of the filtering with each other and calculates the similarity, such as a numerical similarity, between the anatomical objects.

According to the local binary pattern matching method, the medical image registration apparatus 130 defines a relationship between peripheral pixels that surround one center pixel. In other words, the medical image registration apparatus 130 binarizes values of the peripheral pixels with respect to a value of a center pixel. The binarizing helps indicate whether the pixels in the candidate images are similar to one another. The medical image registration apparatus 130 arranges the binary results in a preset direction. As such, by comparing the binary results, the medical image registration apparatus 130 may quantitatively evaluate the similarity between the anatomical objects.

However, the Gabor wavelet method and the local binary pattern method are only examples of candidate methods for calculating similarity. Other embodiments may use different methods for calculating similarity that provide results that are similar to the Gabor wavelet method and the local binary pattern matching method discussed above.

In an embodiment, the medical image registration apparatus 130 selects a 2D medical image having the largest calculated similarity from the 3D medical image. In operation S320, the method generates a coordinate conversion function to convert a first coordinate system used by the first medical apparatus 120 to a second coordinate system used by the second medical apparatus 110 based on the first cross-sectional image and the 2D medical image selected from the 3D medical image.

In operation S320, further, the medical image registration apparatus 130 detects a position corresponding to a coordinate value of the probe 121 of the first medical apparatus 120 in the second coordinate system that is a virtual coordinate system of the second medical apparatus 110. Such a corresponding position is a position in the first coordinate system that is a virtual coordinate system of the first medical apparatus 120 that corresponds to that position in the second coordinate system that is a virtual coordinate system of the second medical apparatus 110.

Referring to FIG. 10, the position corresponding to the position B1 of the probe 121 in the image 1010 corresponds to a position B2 in the medical images 1030. The medical image registration apparatus 130 detects the position B2. The medical image registration apparatus 130 overlays the selected 2D medical image 1033 and the first cross-sectional image 1020 such that the positions of the segmented anatomical objects in the first cross-sectional image 1020 and the 2D medical image 1033 selected in operation S315 are matched, as discussed above.

If the resolutions of the first cross-sectional image 1020 and the 2D medical image 1030 are different from each other, one or both of the images may be up-scaled or down-scaled in order to cause both images to have the same resolution. When the 2D medical image 1033 and the first cross-sectional image 1020 are overlaid with each other, the medical image registration apparatus 130 sets the position B1 of the probe 121 in the 2D medical image 1033 based on the information about the probe location and the coordinate systems. Thus, the medical image registration apparatus 130 detects in the second coordinate system the position B2 corresponding to the position B1 where the probe is located.

The medical image registration apparatus 130 generates a coordinate conversion function to convert the first coordinate system to the second coordinate system by using a coordinate value of the position B2 that is detected. Such a coordinate conversion function is a function that converts a coordinate value of the first coordinate system to a coordinate value of the second coordinate system. The coordinate of the position B2 in the second coordinate system is referred to as $T_{init}$. Then, when the probe 121 is translated and rotated, assuming that the translation of the probe 121 is T(x,y,z) and the rotation of the probe 121 is R(ψ,θ,φ), an example set of matrices that express T(x,y,z) and R(ψ,θ,φ) are provided in Equations 1 and 2 below.

$$T(x, y, z) = \begin{bmatrix} 1 & 0 & 0 & x \\ 0 & 1 & 0 & y \\ 0 & 0 & 1 & z \\ 0 & 0 & 0 & 1 \end{bmatrix} \quad \text{EQUATION 1}$$

$$R_x(\psi)R_y(\theta)R_z(\phi) = \quad \text{EQUATION 2}$$
$$\begin{bmatrix} \cos\theta\cos\psi & \begin{matrix}-\cos\phi\sin\psi + \\ \sin\phi\sin\theta\cos\psi\end{matrix} & \begin{matrix}\sin\phi\sin\psi + \\ \cos\phi\sin\theta\cos\psi\end{matrix} & 0 \\ \cos\theta\sin\psi & \begin{matrix}\cos\phi\cos\psi + \\ \sin\phi\sin\theta\sin\psi\end{matrix} & \begin{matrix}-\sin\phi\cos\psi + \\ \cos\phi\sin\theta\sin\psi\end{matrix} & 0 \\ \sin\theta & \sin\phi\cos\theta & \cos\phi\cos\theta & 0 \\ 0 & 0 & 0 & 1 \end{bmatrix}$$

For example, medical image registration apparatus 130 generates a coordinate conversion function M as shown in Equation 3 by using "$T_{init}$", T(x,y,z) and R(ψ,θ,φ). However, M is merely an example conversion function and similar conversion functions that perform appropriate transformations on the axes to match them with each other may be used in other embodiments.

$$M = R(\psi,\theta,\varphi) * T(x,y,z) * T_{init} \quad \text{EQUATION 3}$$

Referring back to FIG. 2, in operation S210 the method detects a position of the probe 121 of the first medical apparatus 120 from the coordinate system used by the second medical apparatus 110 by using a result of the mapping of the first and second coordinate systems in operation S205. The position of the probe 121 in the first coordinate system may be different from the position of the probe in operation S205. In an embodiment, the probe 121 is in motion as the method proceeds. Thus, in operation S210, when the position of the probe 121 is moved in the first coordinate system, the medical image registration apparatus 130 tracks a movement of the probe 121 in the second coordinate system by using the coordinate conversion function, such as that of Equation 3.

In an embodiment, when the coordinate systems are mapped with each other in operation S205, a change in the real-time medical image according to a physical movement of the probe 121 is tracked in the 3D medical image. To do, the medical image registration apparatus 130 extracts and outputs a cross-sectional image corresponding to the changed real-time medical image according to the physical movement of the probe 121 by using a coordinate value of the probe 121 detected from the second coordinate system.

Figure 4:
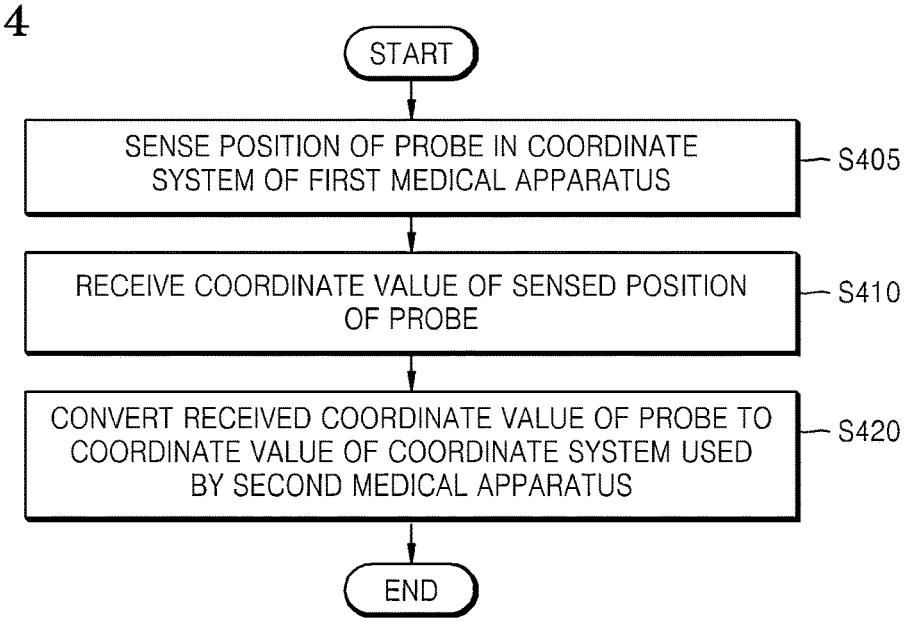
FIG. 4 is a flowchart for explaining a process of detecting a position where a probe of the first medical apparatus is located from the virtual coordinate system used by the second medical apparatus, according to an example embodiment.

Referring further to FIG. 4, in operation S405 the method senses the position of the probe 121 in the first coordinate system used by the first medical apparatus 120. According to one embodiment, the first medical apparatus 120 senses the position of the probe 121, while according to another embodiment, the medical image registration apparatus 130 directly senses the position of the probe 121. In operation S410, the method receives the sensed coordinate value of the probe 121. When the probe 121 is physically moved, the medical image registration apparatus 130 receives a coordinate value of a moved position B3. The coordinate value of the position B3 in the first coordinate system is received separately from or together with the real-time medical image. In operation S420, the method converts the coordinate value of the position B3 in the first coordinate system to a coordinate value of a position B4 in the second coordinate system, such as by using the coordinate conversion function presented in Equation 3, above.

The medical image registration apparatus 130 determines an ultrasound scanning plane of the probe 121 from the position B4 in the second coordinate system. Next, the medical image registration apparatus 130 extracts and outputs a cross-sectional image corresponding to the determined ultrasound scanning plane from the 3D medical image. In an embodiment, the medical image registration apparatus 130 outputs the real-time medical image and the extracted cross-sectional image together. In different embodiments, the extracted cross-sectional image and the real-time medical image may be output as being overlaid with each other or arranged parallel to each other.

Referring back to FIG. 2, in operation S215, the method determines a volume image corresponding to the position of the probe 121 detected from the second coordinate system from the 3D medical image. The volume image corresponding to the position of the probe 121 denotes a 3D medical image existing in a range in which the ultrasound scanning plane of the probe 121 has a relative motion such as with respect to an organ, according to a physical movement, such as due to breathing, of a patient in a state when the probe 121 stands still.

Figure 5:
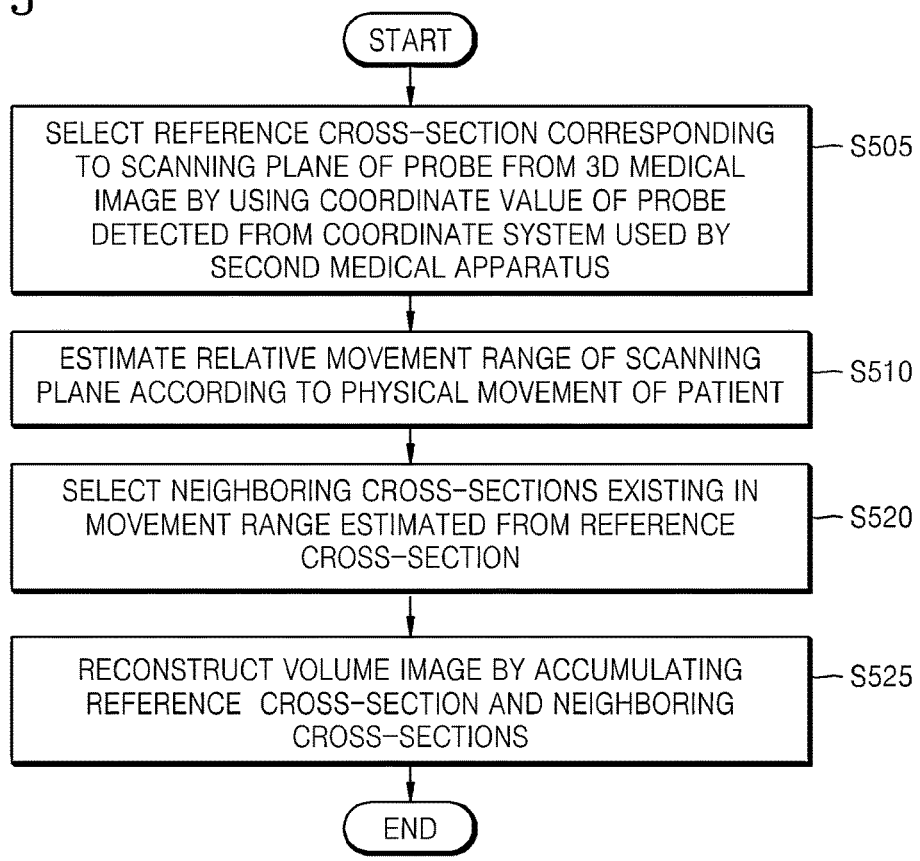
FIGS. 5 and 7 are, respectively, a flowchart and a coordinate system for explaining a process of determining a volume image, according to an example embodiment.
Figure 7:
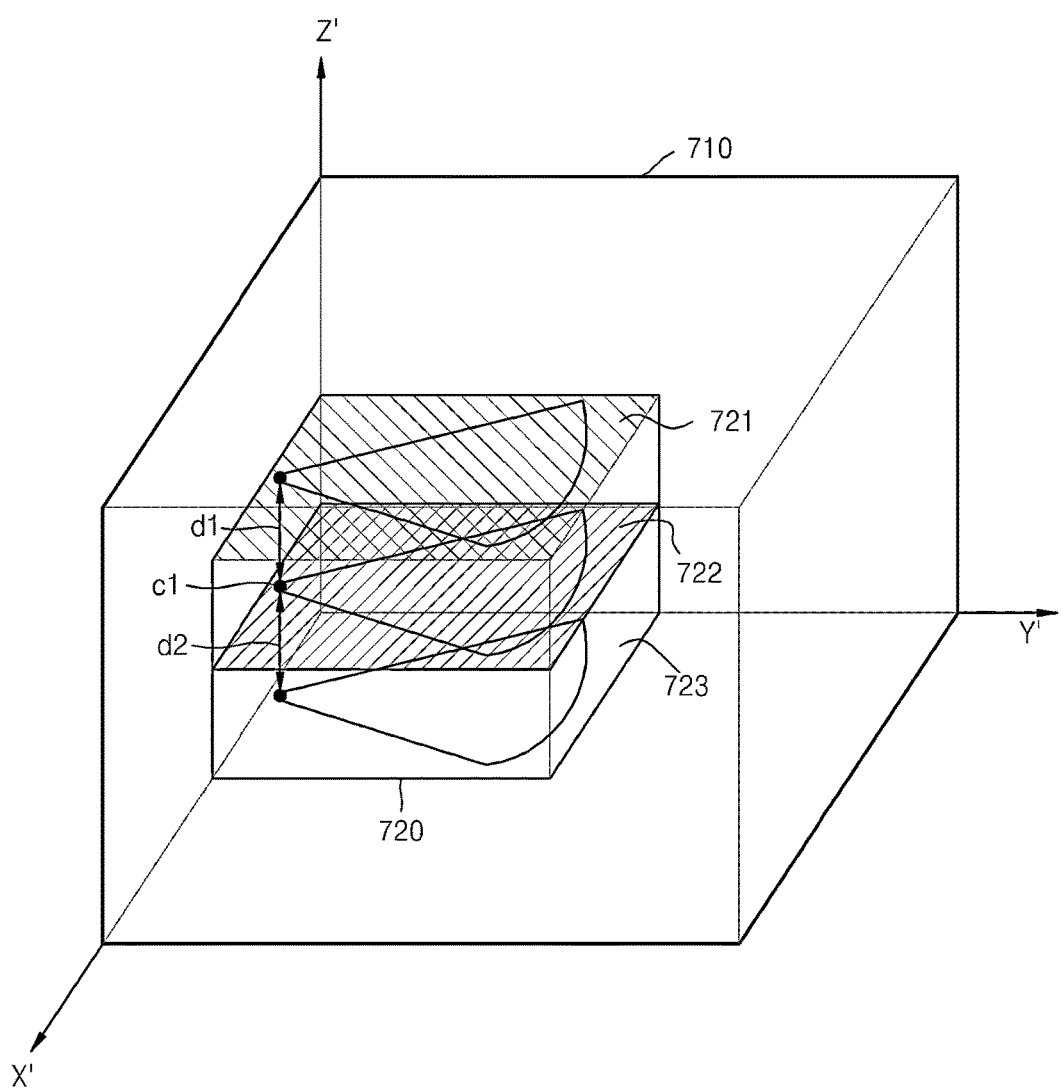

Operation S215 is described in detail with reference to FIGS. 5 and 7. In operation S505, the method selects from the 3D medical image a reference cross-section corresponding to the ultrasound scanning plane of the probe 121 by using the coordinate value of the probe 121 detected from the second coordinate system. In FIG. 7, a cube 710 shows a region where the 3D medical image exists in the second coordinate system. The coordinate value of the probe 121 detected from the second coordinate system is designated to be a position C1. For example, the medical image registration apparatus 130 estimates the ultrasound scanning plane of the probe 121 from the position C1. Next, the medical image registration apparatus 130 selects a reference cross-section 722 including the ultrasound scanning plane of the probe 121.

In operation S510, the method estimates a relative movement range of the ultrasound scanning plane of the probe 121 according to the patient's physical movement. Although the ultrasound scanning plane of the probe 121 does not actually have an absolute physical movement itself, the organ 1110 may move to the position 1120 or the position 1130. Thus, the ultrasound scanning plane of the probe 121 is understood to be relatively moved with respect to the organ 1110.

In an embodiment, the medical image registration apparatus 130 stores previously entered information about a range in which the organ 1110 can be moved by the patient's physical movement. For example, in such an embodiment information that the organ 1110 may be moved a maximum of 40 mm in a direction toward the legend "superior" or "inferior", 12 mm at the maximum in the anterior-posterior direction, and a maximum of 3 mm in the left-right direction is previously stored in the medical image registration apparatus 130 to help interpret relation motion of the organ 1110. However, for convenience of explanation, in the present embodiment, it is assumed that the organ 1110 is moved only in a direction toward the legend "superior" or "inferior". Corresponding approaches apply when the organ 1110 has relative motion in other directions.

The medical image registration apparatus 130 estimates the relative movement range of the ultrasound scanning plane by using the previously stored information. Referring to FIG. 7, the medical image registration apparatus 130 estimates that the ultrasound scanning plane may be moved by a movement range d1 in a +Z' direction that is toward the legend "superior", and by a movement range d2 in a −Z' direction that is toward the legend "inferior". The relative movement of the ultrasound scanning plane is modeled as a relative movement of the position C1.

Referring back to FIG. 5, in operation S520, the method selects neighboring cross-sections 721 and 723 that exist in the movement ranges d1 and d2 estimated from the reference cross-section 722. Although in FIG. 7 only the two neighboring cross-sections 721 and 723 are selected for convenience of explanation, M-number of neighboring cross-sections (M>=2) in addition to the reference cross-section may be selected within the estimated movement ranges d1 and d2.

In operation S525, the method reconstructs a volume image 720 by accumulating the reference cross-section 722 and the neighboring cross-sections 721 and 723. Thus, the volume image 720 is reconstructed from the entire 3D medical image 710 according to the above-described MPR method.

Referring back to FIG. 2, in operation S220, the method extracts from the volume image 720 a cross-sectional image corresponding to the real-time medical image that changes according to the patient's physical movement. As illustrated in FIG. 7, the volume image 720 has a volume smaller than the entire 3D medical image 710. Thus, the time for searching for a cross-sectional view in the volume image 720 is potentially shorter than the time for searching for a cross-sectional image corresponding to the real-time medical image in the 3D medical image 710 because there is less volume to search and hence less data needs to be processed.

The medical image registration apparatus 130 updates the cross-sectional image when the ultrasound scanning plane of the probe 121 is moved by the relative physical movement. In other words, when the ultrasound scanning plane of the probe 121 is moved, the cross-section corresponding to the moved ultrasound scanning plane is extracted again to reflect the movement.

Figure 6:
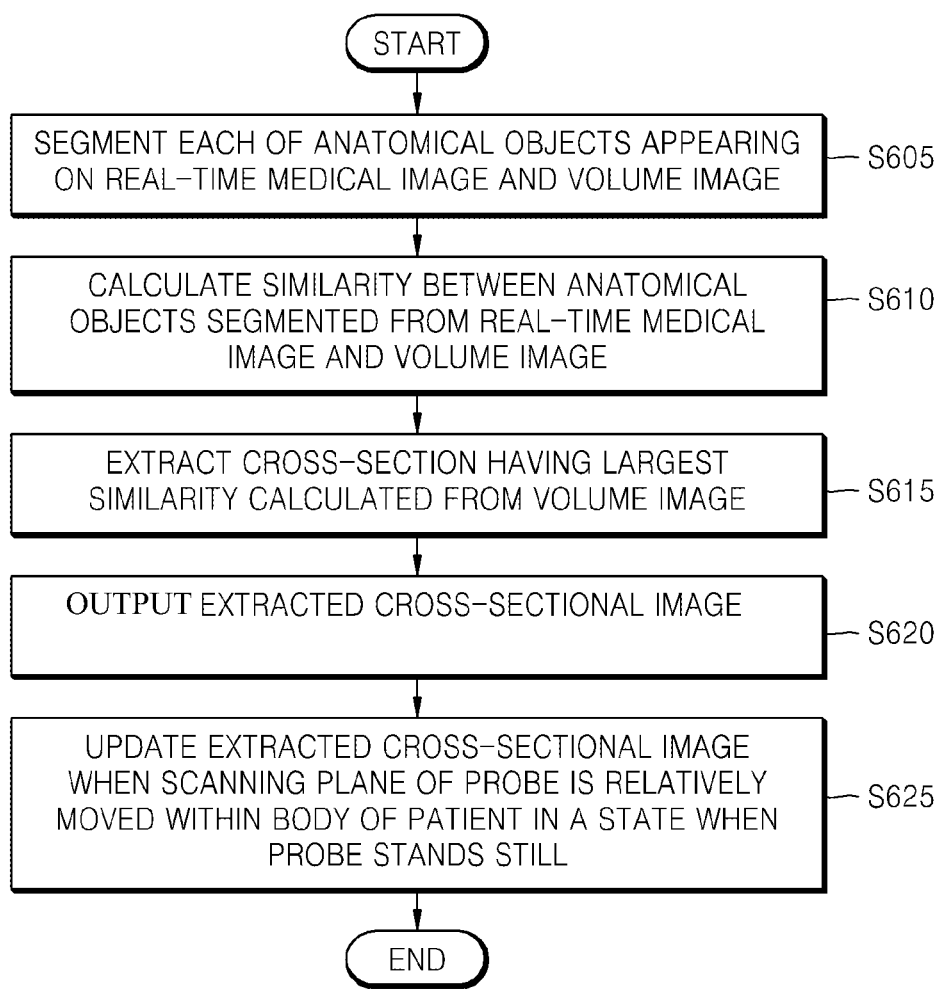
FIG. 6 is a flowchart for explaining a process of extracting a cross-sectional image from a three-dimensional (3D) medical image that considers the patient's physical movement, according to an example embodiment.
Figure 12:
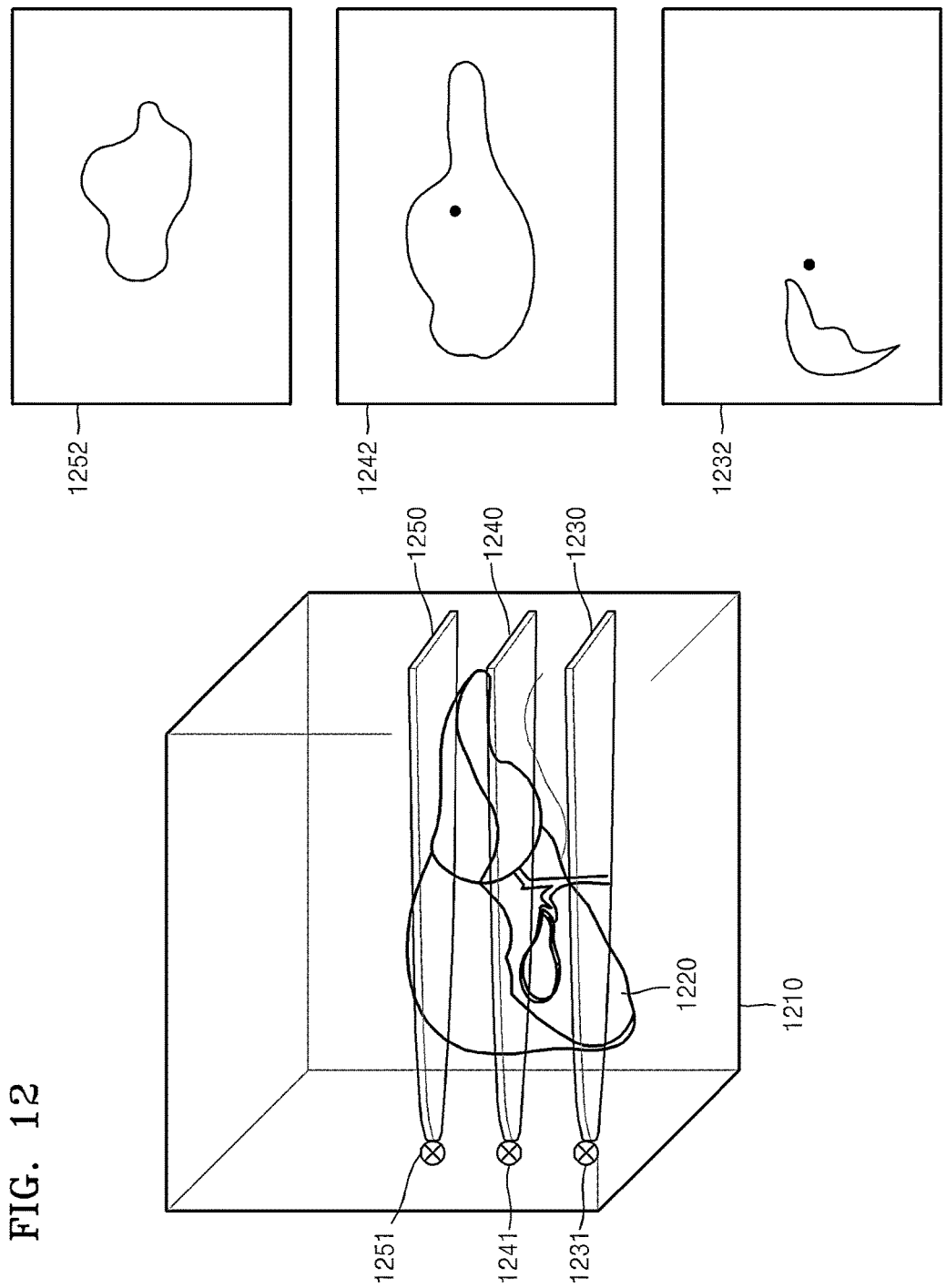

Operation S220 is described further with reference to FIGS. 6 and 12. FIG. 6 is a flowchart for explaining a process of extracting a cross-sectional image from a 3D medical image considering the patient's physical movement, according to an example embodiment.

In operation S605, the method segments each of the anatomic objects appearing on a volume image 1210 and the real-time medical image. For the segmentation, the above-described graph cut method or the GMM method may be used, or other methods that perform appropriate segmentation may be used. The medical image registration apparatus 130 segments the anatomic objects on the volume image 1210 that is modeled in 3D, not 2D. An organ 1220 illustrated in FIG. 12 is an anatomic object segmented from the volume image 1210. Also, the medical image registration apparatus 130 segments the anatomic objects appearing on the real-time medical image.

In operation S610, the method calculates a similarity between the anatomic objects segmented from the real-time medical image and the volume image 1210. The anatomic object 1220 segmented from the volume image 1210 is a 3D object, whereas the anatomic objects segmented from the real-time medical image correspond to 2D objects. Thus, the medical image registration apparatus 130 compares the 3D object and the 2D object to determine how the 3D object and the 2D object compare to one another. In other words, while rotating and moving the 2D object with respect to corresponding portions of the 3D object, the medical image registration apparatus 130 searches for a cross-section most similar to the 2D object in the 3D object. In order to search for a cross-section having the largest similarity, the above-described Gabor wavelet method or the local binary pattern matching method may be used, or other methods that perform appropriate matching may be used.

In operation S615, the method extracts a cross-section having the largest similarity from the volume image 1210. For example, the medical image registration apparatus 130 reconstructs from the volume image 1210 a 2D cross-sectional image corresponding to the cross-section searched for in operation S610.

In operation S620 the method outputs an extracted cross-sectional image. For example, the medical image registration apparatus 130 output the real-time medical image and the extracted cross-sectional image together. The real-time medical image and the extracted cross-sectional image may be output while being overlaid with each other or arranged parallel to each other.

In operation S625, the method updates a cross-sectional image when the ultrasound scanning plane of the probe 121 is relatively moved in the patient's body according to the patient's physical movement in a state when the probe stands still. When the real-time medical image changes in a state when the probe 121 stands still, operations S605 through S620 are repeated. However, since segmentation of the volume image 1210 is already performed in operation S605, the segmentation of the volume image 1210 may be omitted in operation S625.

Referring to FIG. 12, images 1232, 1242, and 1252 schematically illustrate real-time medical images that change according to the patient's physical movement. The real-time medical image 1252 shows an inhalation state, the real-time medical image 1232 shows an exhalation state, and the real-time medical image 1242 shows an intermediate state between the inhalation state and the exhalation state. In FIG. 12, in which segmentation is already performed on the real-time medical images 1232, 1242, and 1252, an organ is indicated by an outline while a blood vessel is indicated by a dot.

As described above, in operation S610, the method searches the volume image 1210 for a cross-section corresponding to the real-time medical image 1252 acquired in the inhalation state. A cross-section 1250 corresponds to the real-time medical image 1252. Thus, the cross-section 1250 corresponds to a virtual ultrasound scanning plane that relatively moves, for example during breathing. Thus, a position 1251 is a position that is derived from a virtual ultrasound scanning plane, not a position where the probe 121 is actually located.

Next, the medical image registration apparatus 130 extracts and outputs a cross-sectional image with respect to the cross-section 1250 from the volume image 1210.

When breathing is in an intermediate state between inhalation and exhalation as time passes, the medical image registration apparatus 130 acquires the real-time medical image 1242 that is changed. The medical image registration apparatus 130 searches for a cross-section 1240 corresponding to the real-time medical image 1242 and updates the cross-sectional image appropriately. In the same process, when it is in the exhalation state, the medical image registration apparatus 130 extracts and outputs a cross-section 1230 corresponding to the real-time medical image 1232 from the volume image 1210.

According to an embodiment, when extracting the cross-sections corresponding to the real-time medical images 1252, 1242, and 1232, the medical image registration apparatus 130 extracts a cross-section from the volume image 1210 by using the coordinate values of the positions 1251, 1241, and 1231. In other words, similarly to a case when the probe 121 is physically moved, the medical image registration apparatus 130 extracts cross-sections corresponding to the real-time medical images 1252, 1242, and 1232 by using the coordinate values of the positions 1251, 1241, and 1231 to match cross-sections with the real-time images.

Figure 8:
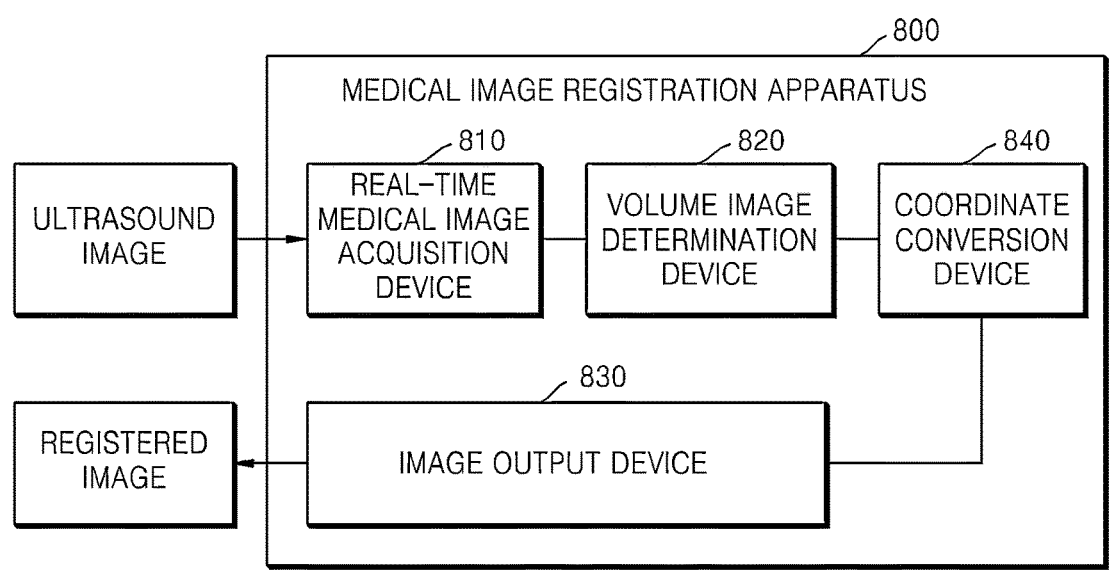
FIGS. 8 and 9 are block diagrams illustrating a medical image registration apparatus, according to an example embodiment.
Figure 9:
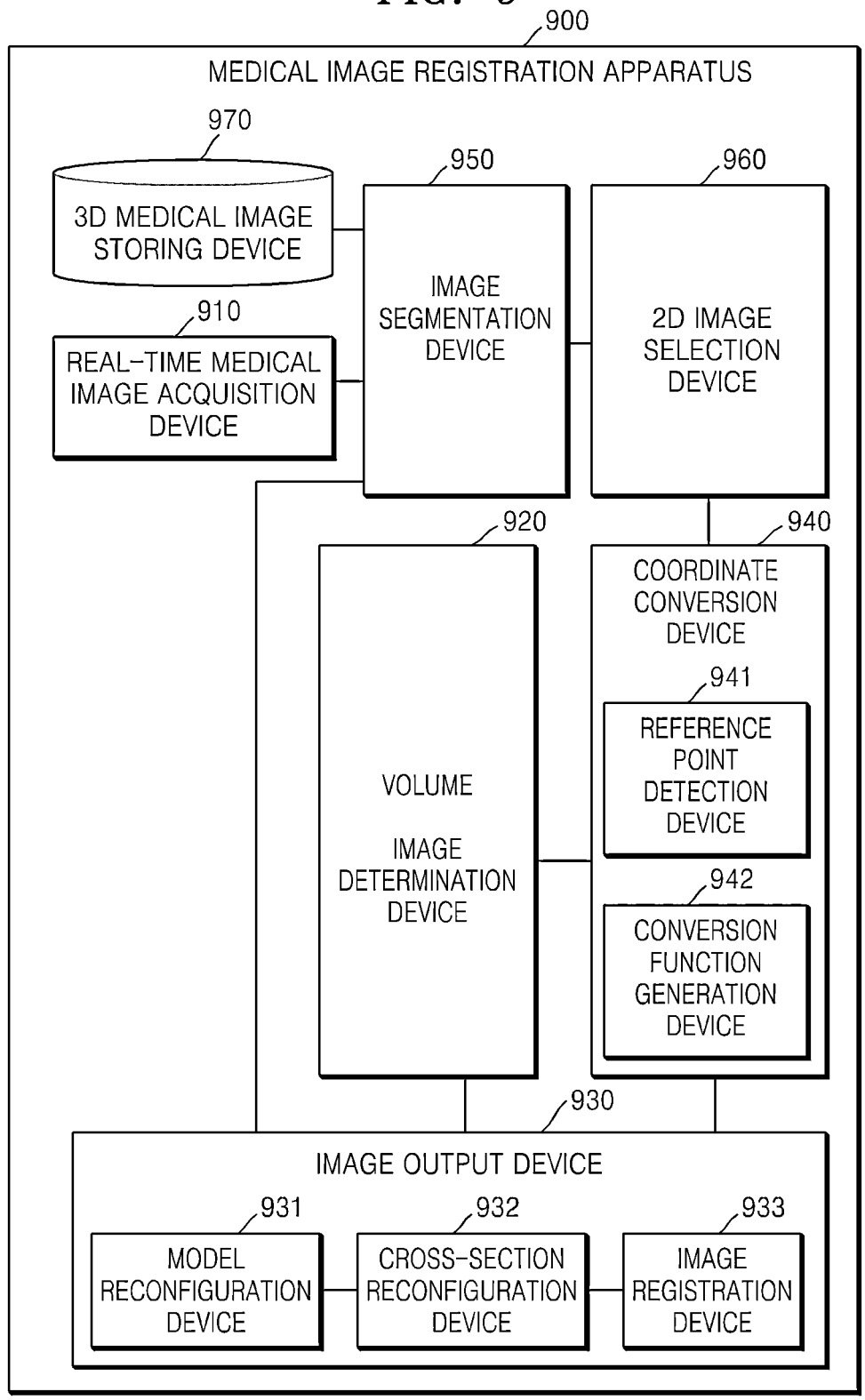

FIGS. 8 and 9 are block diagrams illustrating medical image registration apparatuses 800 and 900 according to example embodiments. Since the medical image registration apparatuses 800 and 900 of FIGS. 8 and 9 are apparatuses performing the above-described method of performing registration of medical images, descriptions that are the same as those above will be omitted. Thus, the above descriptions may be referred to with respect to the embodiments of FIGS. 8 and 9.

Referring to FIG. 8, the medical image registration apparatus 800 includes a real-time medical image acquisition device 810, a volume image determination device 820, a coordinate conversion device 840, and an image output device 830. The real-time medical image acquisition device 810 acquires a real-time medical image captured by the first medical apparatus 120. The real-time medical image acquisition device 810 periodically acquires a real-time medical image from the first medical apparatus 120.

The coordinate conversion device 840 maps the first coordinate system used by the first medical apparatus 120 and the second coordinate system used by the second medical apparatus 110. The coordinate conversion device 840 detects the position of the probe 121 of the first medical apparatus 120 in the second coordinate system by using a result of the mapping of the coordinate systems.

The volume image determination device 820 determines a volume image corresponding to the position of the probe 121 detected from the second coordinate system, from the 3D medical image previously captured by the second medical apparatus 110. The image output device 830 extracts from the volume image a cross-sectional image corresponding to a real-time medical image that changes according to the patient's physical movement. The image output device 830 updates a cross-sectional image when the ultrasound scanning plane of the probe 121 is relatively moved in the patient's body according to the patient's physical movement.

FIG. 9 is a block diagram illustrating the medical image registration apparatus 900 according to another example embodiment. Referring to FIG. 9, the medical image registration apparatus 900 includes a real-time medical image acquisition device 910, a volume image determination device 920, an image output device 930, a coordinate conversion device 940, an image segmentation device 950, a 2D image selection device 960, and a 3D medical image storing device 970. The same descriptions as those about the embodiment of FIG. 9, presented above, are omitted.

The 3D medical image storing device 970 stores a 3D medical image captured by the second medical apparatus 110 before a medical operation. The stored 3D medical image includes a set of a plurality of 2D medical images. In an embodiment, each of the 2D medical images is mapped with coordinate values indicating positions in the second coordinate system.

The 2D image selection device 960 generates a first cross-sectional image of a real-time medical image. The 2D image selection device 960 also selects a 2D medical image corresponding to the first cross-sectional image among the 2D medical images forming the 3D medical image, based on the anatomical feature appearing on the first cross-sectional image. The above-described segmentation is performed to compare and match the anatomical feature appearing on the first cross-sectional image and the 3D medical image.

The image segmentation device 950 segments each of the anatomical features appearing on the first cross-sectional image and the anatomical features appearing on the 3D medical image. In an embodiment, information about the anatomical object to be segmented is previously stored in the image segmentation device 950. For example, the image segmentation device 950 may perform segmentation by using the graph cut method or the GMM method, or another segmentation method, as discussed above.

The 2D image selection device 960 calculates a similarity between the segmented anatomical objects of the first cross-sectional image and the segmented anatomical objects of the 3D medical image. The 2D image selection device 960 may calculate the similarity by using the Gabor wavelet method or the local binary pattern matching method, or another matching method, as discussed above. The 2D image selection device 960 selects a 2D medical image having the largest similarity calculated to the 3D medical image.

The coordinate conversion device 940 includes a reference point detection device 941 and a conversion function generation device 942. The reference point detection device 941 detects the position B2 corresponding to the position B1 where the probe 121 of the first medical apparatus 120 is located in the virtual coordinate system of the first medical apparatus 120, from the virtual coordinate system of the second medical apparatus 110. The conversion function generation device 942 generates a coordinate conversion function to convert a virtual coordinate system of the first medical apparatus 120 to the virtual coordinate system of the first medical apparatus 120 by using the coordinate value of the position B2. An example coordinate conversion function is presented as Equation 3.

When the probe 121 is physically moved, the coordinate conversion device 940 receives a coordinate value of the probe 121 moved in the coordinate system used by the first medical apparatus 120. The coordinate conversion device 940 converts the coordinate value of the probe 121 that is moved to a coordinate value of the coordinate system used by the second medical apparatus 110 by using a mapping result, such as from a coordinate conversion function.

When the coordinate conversion function is generated, a change in the real-time medical image according to a physical movement of the probe 121 may be tracked on the 3D medical image. Thus, the medical image registration apparatus 900 extracts and outputs a cross-sectional image corresponding to the changed real-time medical image according to the physical movement of the probe 121, by using the coordinate value of the probe 121 detected in the second coordinate system.

The volume image determination device 920 determines a volume image corresponding to the position of the probe 121 detected in the second coordinate system, from the 3D medical image. The volume image corresponding to the position of the probe 121 signifies a 3D medical image existing in a range in which the ultrasound scanning plane of the probe 121 relatively moves with respect to an organ according to a physical movement, such as breathing, of a patient in a state when the probe 121 stands still.

The volume image determination device 920 selects a reference cross-section corresponding to the ultrasound scanning plane of the probe 121 from the 3D medical image by using the coordinate value of the probe 121 detected in the second coordinate system. The volume image determination device 920 estimates a relative movement range of a scanning plane of the probe 121, according to the patient's physical movement, when the probe 121 stands still. For example, the volume image determination device 920 determines the size of a volume image from the 3D medical image based on an estimated movement range.

The volume image determination device 920 selects the reference cross-section corresponding to the scanning plane of the probe 121 from the 3D medical image by using the coordinate value of the position of the probe 121 detected in the second coordinate system and selects the reference cross-section and cross-sections neighboring the reference cross-section from the 3D medical image. In an embodiment, a model reconfiguration device 931 reconfigures the volume image by accumulating the cross-sections neighboring the reference cross-section.

The image output device 930 extracts a cross-sectional image corresponding to the real-time medical image, that changes according to the patient's physical movement, from the volume image. The image output device 930 extracts the cross-sectional image based on the similarity of the anatomical objects appearing on the real-time medical image and the determined volume image. The image output device 930 updates the cross-sectional image when the ultrasound scanning plane of the probe 121 is relatively moved in the patient's body according to the patient' physical movement.

For the extraction of a cross-sectional image, the image output device 930 requests for the image segmentation device 950 to perform segmentation on each of the anatomical objects appearing on the real-time medical image and the volume image. Next, the image output device 930 extracts a cross-section having the largest similarity between the anatomical objects segmented from the real-time medical image and the volume image. To search for the cross-section having the largest similarity, the above-described Gabor wavelet method or local binary pattern matching method, or other appropriate methods may be used.

In an embodiment, the image output device 930 includes the model reconfiguration device 931, a cross-section reconfiguration device 932, and an image registration device 933. The model reconfiguration device 931 reconfigures a 3D model by using a set of the second medical images captured by the second medical apparatus 110 that define the 3D medical image. The model reconfiguration device 931 reconfigures the volume image determined by the volume image determination device 920 from the 3D medical image, into a 3D model.

The cross-section reconfiguration device 932 reconfigures a cross-sectional image from the 3D model reconfigured by the model reconfiguration device 931. Thus, the cross-section reconfiguration device 932 extracts image data about a cross-section crossing the 3D model from the 3D model and reconfigures the extracted image data into a cross-sectional image. The reason for the change of a real-time medical image may include the physical movement of the probe 121 or the patient's physical movement, as described above.

The image registration device 933 registers the real-time medical image and the cross-sectional image extracted from the 3D medical image and outputs the registered image. During the output, the cross-sectional image and the real-time medical image may be output being overlaid or arranged parallel to each other.

In an embodiment, the image output by the image output device 930 is displayed on the image display apparatus 140, such as a monitor. The image display apparatus 140 may be implemented as a liquid crystal display (LCD), a light-emitting diode (LED) display, a plasma display panel (PDP), a screen, a terminal, and the like. A screen may be a physical structure that includes one or more hardware components that provide the ability to render a user interface and/or receive user input. The screen can encompass any combination of display region, gesture capture region, a touch sensitive display, and/or a configurable area. The screen can be embedded in the hardware or may be an external peripheral device that may be attached and detached from the apparatus. The display may be a single-screen or a multi-screen display. A single physical screen can include multiple displays that are managed as separate logical displays permitting different content to be displayed on separate displays although part of the same physical screen.

As described above, according to the various embodiments, the real-time medical image is registered with the 3D medical image of the second medical apparatus in consideration of both changes in the real-time medical image according to the physical movement of the probe of the first medical apparatus and a changes in the real-time medical image according to the physical movement of the patient while the probe remains still, a more accurate registered image is acquired. Also, since the registration of medical images is automated, registration may be quickly performed. Thus, by performing registration as discussed in the application, it is possible to take advantage of the real-time aspects of imaging technologies such as ultrasound while also taking advantage of the higher image quality of other imaging technologies such as CT or MR imaging that are not well-suited for real-time imaging.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

A computing system or a computer may include a microprocessor that is electrically connected to a bus, a user interface, and a memory controller, and may further include a flash memory device. The flash memory device may store N-bit data via the memory controller. The N-bit data may be data that has been processed and/or is to be processed by the microprocessor, and N may be an integer equal to or greater than 1. If the computing system or computer is a mobile device, a battery may be provided to supply power to operate the computing system or computer. It will be apparent to one of ordinary skill in the art that the computing system or computer may further include an application chipset, a camera image processor, a mobile Dynamic Random Access Memory (DRAM), and any other device known to one of ordinary skill in the art to be included in a computing system or computer. The memory controller and the flash memory device may constitute a solid-state drive or disk (SSD) that uses a non-volatile memory to store data.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of performing registration of medical images, comprising:
    mapping, by a processor, a virtual coordinate system used by a first medical apparatus and a virtual coordinate system used by a second medical apparatus to each other, wherein a real-time medical image is captured in a first position of a patient by the first medical apparatus and a three-dimensional (3D) medical image is previously captured in a second position of the patient by the second medical apparatus;
    detecting, by the processor, a position of a probe of the first medical apparatus in the virtual coordinate system used by the second medical apparatus, based on a result of the mapping;
    determining, by the processor, a volume image, corresponding to the detected position of the probe, from the previously captured 3D medical image;
    selecting a reference cross-section from the determined volume image using the detected position of the probe;
    estimating a relative movement range of a scanning plane of the probe from the reference cross-section according to a patient's physical movement with the probe being static relative to the virtual coordinate system used by the second medical apparatus and by using previously stored information about a range in which an organ can be moved by the patient's physical movement;
    selecting neighboring cross-sections that exist in the estimated relative movement range of the scanning plane;
    reconstructing a volume image by accumulating the reference cross-section and the neighboring cross-sections; and
    extracting, by the processor, from the reconstructed volume image a cross-sectional image corresponding to the real-time medical image, wherein the cross-sectional image changes according to the patient's physical movement, and
    wherein the determined volume image comprises a volume image smaller than the previously captured 3D medical image and has a dimension determined by the estimated relative movement range of the scanning plane of the probe from the reference cross-section.

2. The method of claim 1, wherein, in the extracting of the cross-sectional image, the cross-sectional image is updated when the scanning plane of the probe is moved relative to the patient's body according to the patient's physical movement.

3. The method of claim 1, wherein the mapping of the virtual coordinate systems comprises:
    generating a first cross-sectional image of the real-time medical image;
    selecting a two-dimensional (2D) medical image corresponding to the first cross-sectional image among a plurality of 2D medical images forming the 3D medical image based on an anatomical feature appearing in the first cross-sectional image; and generating a coordinate conversion function to convert the coordinate system used by the first medical apparatus to the coordinate system used by the second medical apparatus based on the selected 2D medical image and the first cross-sectional image.

4. The method of claim 1, wherein the detecting of the position of the probe comprises:
receiving a coordinate value of the probe that is moved in the coordinate system used by the first medical apparatus, when the probe is moved; and
converting the coordinate value of the probe that is moved to a coordinate value of the coordinate system used by the second medical apparatus, by using the mapping result.

5. The method of claim 1, wherein the extracting of the cross-sectional image comprises:
acquiring a real-time medical image that changes in a state when the probe remains still; and
extracting the cross-sectional image considering an anatomical feature appearing on the acquired real-time medical image.

6. A non-transitory computer-readable storage medium storing instructions that, when executed by a processor, cause the processor to perform a method of registration of medical images, the method comprising:
mapping a virtual coordinate system used by a first medical apparatus and a virtual coordinate system used by a second medical apparatus to each other, wherein a real-time medical image is captured in a first position of a patient by the first medical apparatus and a three-dimensional (3D) medical image is previously captured in a second position of the patient by the second medical apparatus;
detecting a position of a probe of the first medical apparatus in the virtual coordinate system used by the second medical apparatus, based on a result of the mapping;
determining a volume image, corresponding to the detected position of the probe, from the previously captured 3D medical image;
selecting a reference cross-section from the determined volume image using the detected position of the probe;
estimating a relative movement range of a scanning plane of the probe from the reference cross-section according to a patient's physical movement with the probe being static relative to the virtual coordinate system used by the second medical apparatus and by using previously stored information about a range in which an organ can be moved by the patient's physical movement;
selecting neighboring cross-sections that exist in the estimated relative movement range of the scanning plane;
reconstructing a volume image by accumulating the reference cross-section and the neighboring cross-sections; and
extracting, by the processor, from the reconstructed volume image a cross-sectional image corresponding to the real-time medical image, wherein the cross-sectional image changes according to the patient's physical movement, and
wherein the determined volume image comprises a volume image smaller than the previously captured 3D-medical image and has a dimension determined by the estimated relative movement range of the scanning plane of the probe from the reference cross-section.

7. An apparatus for performing registration of medical images comprising:
a processor configured to:
map a virtual coordinate system used by a first medical apparatus and a virtual coordinate system by a second medical apparatus to each other, and detect a position of a probe of the first medical apparatus in the virtual coordinate system used by the second medical apparatus based on a result of the mapping;
determine a volume image corresponding to the detected position from a previously captured 3D medical image;
select a reference cross-section from the determined volume image using the detected position of the probe;
estimate a relative movement range of a scanning plane of the probe from the reference cross-section according to a patient's physical movement with the probe being static relative to the virtual coordinate system used by the second medical apparatus and by using previously stored information about a range in which an organ can be moved by the patient's physical movement;
select neighboring cross-sections that exist in the estimated relative movement range of the scanning plane;
reconstruct a volume image by accumulating the reference cross-section and the neighboring cross-sections; and
extract from the reconstructed volume image a cross-sectional image corresponding to a real-time medical image, wherein the cross-sectional image changes according to the patient's physical movement, and
wherein the determined volume image comprises a volume image smaller than the previously captured 3D medical image and has a dimension determined by the estimated relative movement range of the scanning plane of the probe from the reference cross-section.

8. The apparatus of claim 7, wherein the cross-sectional image is updated when the scanning plane of the probe is moved relative to a patient's body according to the patient's physical movement.

9. The apparatus of claim 7, wherein the processor is further configured to generate a first cross-sectional image of the real-time medical image, select a 2D medical image corresponding to the first cross-sectional image among a plurality of 2D medical images forming the 3D medical image based on an anatomical feature appearing in the first cross-sectional image, and generate a coordinate conversion function to convert a coordinate system used by the first medical apparatus to the coordinate system used by the second medical apparatus based on a selected 2D medical image and the first cross-sectional image.

10. The apparatus of claim 7, wherein, when the probe is moved, the processor receives a coordinate value of the probe that is moved in the coordinate system used by the first medical apparatus, and converts the coordinate value of the probe that is moved to a coordinate value of the coordinate system used by the second medical apparatus, by using the mapping result.

11. The apparatus of claim 7, wherein the processor is further configured to acquire the real-time medical image captured by the first medical apparatus.

12. The method of claim 1, wherein the extracting of the cross-sectional image comprises extracting the cross-sectional image based on a similarity between anatomical features appearing on the real-time medical image and the determined volume image.

13. The method of claim 1, wherein the extracting of the cross-sectional image comprises:

performing segmentation on each of anatomical objects appearing on the real-time medical image and the cross-sectional images of the determined volume image; and extracting from the determined volume image a selected cross-sectional image of the cross-sectional images having a largest similarity between the anatomical objects segmented in the real-time medical image and anatomical objects in the selected cross-sectional image of the determined volume image.

14. The apparatus of claim 7, wherein the processor is further configured to extract the cross-sectional image based on a similarity between anatomical features appearing on the real-time medical image and the determined volume image.

15. The apparatus of claim 7, wherein the processor is further configured to perform segmentation on each of anatomical objects appearing on the real-time medical image and the volume image, and extract from the volume image a cross-section having a largest similarity between the anatomical objects segmented in the real-time medical image and the volume image.

* * * * *